(12) United States Patent
Michot et al.

(10) Patent No.: US 6,620,546 B1
(45) Date of Patent: Sep. 16, 2003

(54) MATERIALS FOR USE AS ELECTROLYTIC SOLUTES

(75) Inventors: Christophe Michot, Grenoble (FR); Michel Armand, Montreal (CA); Yves Choquette, Sainte-Julie (CA); Michel Gauthier, La Prairie (CA)

(73) Assignees: ACEP Inc., Montreal (CA); Universite de Montreal, Montreal (CA); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/355,454

(22) PCT Filed: Dec. 1, 1998

(86) PCT No.: PCT/FR98/02585

§ 371 (c)(1),
(2), (4) Date: Sep. 24, 1999

(87) PCT Pub. No.: WO99/28292

PCT Pub. Date: Jun. 10, 1999

(30) Foreign Application Priority Data

Dec. 1, 1997 (CA) .............................................. 2224046
Feb. 3, 1998 (CA) .............................................. 2228801

(51) Int. Cl.[7] .................... H01M 6/16; C07C 309/00
(52) U.S. Cl. .................... 429/188; 429/199; 252/62.2; 564/96
(58) Field of Search .................... 429/188, 199, 429/200; 252/62.2, 500; 564/96, 98

(56) References Cited

U.S. PATENT DOCUMENTS

| | | |
|---|---|---|
| 3,793,079 A | 2/1974 | Brown et al. |
| 4,851,307 A | 7/1989 | Armand et al. |
| 5,072,040 A | 12/1991 | Armand |
| 5,273,840 A | 12/1993 | Dominey |
| 5,446,134 A | 8/1995 | Armand et al. |
| 5,502,251 A | 3/1996 | Pohmer et al. |
| 5,514,493 A | 5/1996 | Waddell et al. |
| 5,538,812 A | 7/1996 | Lee et al. |
| 5,609,990 A | 3/1997 | Ha et al. |
| 5,654,112 A | 8/1997 | Itou et al. |
| 5,691,081 A | 11/1997 | Krause et al. |
| 5,817,376 A | 10/1998 | Everaerts et al. |
| 5,874,616 A | 2/1999 | Howells et al. |
| 5,962,546 A | 10/1999 | Everaerts et al. |
| 6,063,522 A | 5/2000 | Hamrock et al. |

FOREIGN PATENT DOCUMENTS

| | | |
|---|---|---|
| EP | 0 571 832 | 5/1993 |
| EP | 0 850 921 | 7/1998 |
| EP | 0 850 932 | 7/1998 |
| WO | WO 96/24928 | 8/1996 |
| WO | WO 96/24929 | 8/1996 |
| WO | WO 97/23448 | 7/1997 |
| WO | WO 97/35929 | 10/1997 |
| WO | WO 97/35930 | 10/1997 |
| WO | WO 98/50349 | 11/1998 |
| WO | WO 99/49529 | 9/1999 |
| WO | WO 00/10969 | 3/2000 |
| WO | WO 00/11742 | 3/2000 |

OTHER PUBLICATIONS

Chemical Abstracts, vol. 88, No. 18, May 1, 1978, Abstract No. 130067e, XP002097853.

*Primary Examiner*—Patrick Ryan
*Assistant Examiner*—Tracy Dove
(74) *Attorney, Agent, or Firm*—Choate, Hall & Stewart

(57) ABSTRACT

The invention relates to ionic compositions having a high ionic conductivity comprising a salt with a delocalized anionic charge.

An ionic composition comprises a salt in solution in a solvent and has a conductivity of greater than $10^{-5}$ S.cm$^{-1}$ between $-30°$ C. and $150°$ C. The cation is a proton, a hydronium, a hydroxonium, a nitrosonium NO$^+$, an ammonium NH$_4^+$ or a metal, organic or organometallic cation. The anion is a carbanion carrying a perfluorinated substituent or a substituent carrying at least one F on the carbon α to the carbanion and two nonperfluorinated electron-withdrawing substituents.

Use as electrolyte in electrochemical devices, as catalyst of chemical reactions, or as photochemical or thermochemical initiator for polymerization or crosslinking reactions.

49 Claims, No Drawings

MATERIALS FOR USE AS ELECTROLYTIC SOLUTES

BACKGROUND OF THE INVENTION

1. Field of the Invention

The subject-matter of the present invention is ionic compositions having a high ionic conductivity, comprising a salt in which the anionic charge is delocalized, and their uses, in particular as electrolyte.

2. Description of the Related Art

It is known and particularly advantageous to introduce ionic groups into organic molecules or polymers having various functions. This is because the coulombic forces correspond to the strongest available interactions at the molecular level and the ionic groups modify in the most pronounced way the molecules to which they are attached. Mention may be made of dyes, which are rendered soluble in water using sulfonate or carboxylate functional groups.

However, the groups of this type, $—CO_2^-$ $1/mM^{m+}$ or $—SO_3^-$ $1/mM^{m+}$, are not dissociated and they do not induce solubility in solvents other than water or some very polar protic solvents, such as light alcohols, which greatly restrict the scope of their use.

Furthermore, salts of the compounds $1/mM^{m+}$ $C^-(SO_2R_F)_3$, in which $R_F$ is a perfluorinated group and $M^{m+}$ a cation with the valency m, are known which are soluble and dissociated in organic aprotic media or in solvating polymers. However, it is considered that the existence of at least two perfluoroalkylsulfonyl groups (in particular the existence of fluorine atoms on the carbon atom α to each of the sulfonyl groups), which exert a large attractant power on the electrons of the anionic charge, is a necessary condition for the solubility and dissociation properties to be obtained.

SUMMARY OF THE INVENTION

Surprisingly, the inventors have found that the excellent solubility and dissociation properties of the $^-C(SO_2R_F)_3$ ionic groups are retained when a single sulfone group has fluorine atoms on atoms adjacent to the sulfur atom, allowing an extremely wide choice of functional molecules. In just as unexpected a way, it was found that it is possible, with the same properties being obtained, to omit the $—SO_2—$ group attached to the nonperfluorinated group, provided that the group attached directly to the carbon has a Hammett parameter σ* of greater than 0.55. By way of comparison, the Hammett parameter σ* of an $—SO_2—$ group connected to a nonperfluorinated group is 3.5 and 4.55 for a $CF_3SO_2—$ group.

The subject-matter of the present invention is an ionic composition comprising at least one ionic compound in solution in a solvent, the said ionic compound comprising an anionic part associated with at least one cationic part $M^{m+}$ in a number sufficient to ensure the electronic neutrality of the combination. The said composition is characterized in that it has a conductivity of greater than $10^{-5}$ S.cm$^{-1}$ at a temperature of between −30° C. and 150° C, in that $M^{m+}$ is a proton, a hydronium, a hydroxonium, a nitrosonium $NO^+$, an ammonium $—NH_4^+$ or a cation having the valency m chosen from metal cations, organic cations and organometallic cations, and in that the anionic part corresponds to one of the formulae $X_F—SO_x—C^-(Z)(Z')$, $X_F—SO_x—C^-(YR)(Y'R')$ or $X_F—SO_x—C^-—(Z)(YR)$ in which:

x is 2 (sulfonyl group) or 1 (sulfinyl group)

$X_F$ represents a monovalent or multivalent radical chosen from the group consisting of linear, branched or cyclic perhalogenated radicals of the alkyl, alkylaryl, oxa-alkyl, aza-alkyl, thia-alkyl, alkenyl, oxa-alkenyl, aza-alkenyl, thia-alkenyl or dialkylazo type or from the group consisting of organic radicals in which the carbon α to the $SO_x$ group carries at least one F atom, it being understood that a multivalent $X_F$ radical is connected to more than one $—SO_xC—$ group;

Z and Z' represent, independently of one another, a monovalent or multivalent electron-withdrawing radical, it being understood that a multivalent Z or Z' radical can form part of a ring or be connected to several $—C^-SO_x—X_F—$ groups;

Y or Y' represent a sulfonyl, sulfinyl, carbonyl or phosphonyl group;

R is a monovalent or multivalent organic radical and R' is H or a monovalent or multivalent organic radical, R and R' being other than a perfluoroalkyl when x=2; it being understood that each of the substituents R, R', Z or Z' can form part of an aromatic or nonaromatic ring or of a polymer, and that each of the substituents $X_F$, R, R', Z or Z' can be connected to a substituent $X_F$, R, R', Z or Z' carried by the same anionic center $C^-$ or by another anionic center.

DETAILED DESCRIPTION OF THE PREFERRED EMBODIMENTS

In the ionic compound of a composition of the present invention, the cation can be a metal cation chosen from alkali metal cations, alkaline earth metal cations, transition metal cations, in the divalent or trivalent state, and rare earth cations. Mention may be made, by way of example, of $Na^+$, $Li^+$, $K^+$, $Sm^{3+}$, $La^{3+}$, $Ho^{3+}$, $Sc^{3+}$, $Al^{3+}$, $Y^{3+}$, $Yb^{3+}$, $Lu^{3+}$ or $Eu^{3+}$.

The cation can also be an organometallic cation, in particular a metallocenium. Mention may be made, by way of example, of the cations derived from ferrocene, from titanocene, from zirconocene, from an indenocenium or from a metallocenium arene, the cations of transition metals complexed by ligands of phosphine type optionally possessing a chirality, or the organometallic cations possessing one or more alkyl or aryl groups covalently attached to an atom or a group of atoms, such as the methylzinc, phenylmercury, trialkyltin or trialkyllead cations. The organometallic cation can form part of a polymer chain.

The cation of the salt of a composition of the invention can be an organic cation chosen from the group consisting of the $R''_3O^+$ (onium), $NR''_4^+$ (ammonium), $R''C(NHR''_2)_2^+$ (amidinium), C $(NHR''_2)_3^+$ (guanidinium), $C_5R''_6N^+$ (pyridinium), $C_3R''_5N_2^+$ (imidazolium), $C_2R''_4N_3^+$ (triazolium), $C_3R''_7N_2^+$ (imidazolinium), $SR''_3^+$ (sulfonium), $PR''_4^+$ (phosphonium), $IR''_2^+$ (iodonium) or $(C_6R''_5)_3C^+$ (carbonium) cations, the R'' radicals independently representing H or a nonperfluorinated organic radical. The organic radicals R'', which are identical or different, are preferably chosen from the group consisting of the proton, alkyl, alkenyl, oxa-alkyl, oxa-alkenyl, aza-alkyl, aza-alkenyl, thia-alkyl, thia-alkenyl, optionally hydrolyzable sila-alkyl or optionally hydrolyzable sila-alkenyl radicals and dialkylazo radicals, it being possible for the said radicals to be linear, branched or cyclic;

cyclic or heterocyclic radicals optionally comprising at least one side chain comprising heteroatoms, such as nitrogen, oxygen or sulfur;

aryl groups, arylalkyl groups, alkylaryl groups and alkenylaryl groups optionally comprising heteroatoms in the aromatic nucleus or in a substituent;

groups comprising several condensed or noncondensed, aromatic or heterocyclic nuclei, optionally comprising at least one nitrogen, oxygen, sulfur or phosphorus atom. When an onium cation carries at least two R'' radicals other than H, these radicals can together form an aromatic or nonaromatic ring, optionally encompassing the center carrying the cationic charge.

A cationic onium group can be polycationic, for example when an R'' substituent is a divalent substituent connected to two cationic centers. Mention may be made, by way of example, of the cation of the following compound activated by a source of actinic energy of appropriate wavelength. Mention may be made, as specific examples of such salts, of substituted or unsubstituted phenacyldialkylsulfonium, trialkylaryl-sulfonium, triarylsulfonium, dialkylaryliodonium and diaryliodonium salts. The abovementioned cations can form part of a polymer chain.

The M cation of a salt can incorporate a 2,2'[Azobis(2-2'-imidazolinio-2-yl)propane]$^{2+}$ or 2,2'-Azobis(2-amidiniopropane)$^{2+}$ group. The salt is then capable of releasing, under the action of heat or of ionizing radiation,

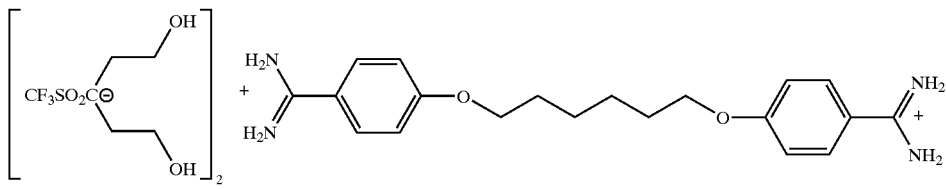

When the cationic part of the ionic compound is an onium cation, it can be provided either in the form of an independent cationic group which is only bonded to the anionic part via the ionic bond between the positive charge of the cation and the negative charge of the anionic part. In this case, the cationic part can form part of a repeat unit of a polymer.

An onium cation can also form part of one of the $R^H$, R or R' radicals. In this case, the ionic compound constitutes a zwitterion. Mention may be made, by way of example, of the following compound:

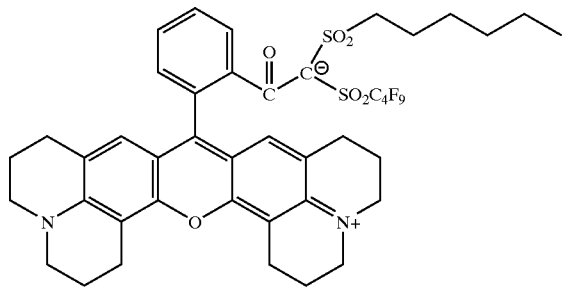

The onium cation can be chosen so as to introduce, into the salt, substituents which make it possible to confer specific properties on the said salt. For example, the M$^+$ cation can be a cationic heterocycle of aromatic nature comprising at least one quaternized nitrogen atom in the ring. Mention may be made, by way of example, of the imidazolium, triazolium, pyridinium and 4-(dimethylamino)pyridinium ions, the said cations optionally carrying a substituent on the carbon atoms of the ring. Among these cations, those which give a salt with a melting point of less than 150° C. are advantageous, because they give ionic compositions which have a protonic conduction. A particularly preferred composition with protonic conduction comprises a salt in which the cation is formed by addition of a proton to the nitrogen of an imidazoline, of an imidazole or of a triazole, as well as the corresponding nitrogenous base, in a proportion of 0.5 to 10 by molar ratio.

A salt in which the cation is a cationic group possessing an —N=N— or ~N≡N$^+$ linkage, a sulfonium group, an iodonium group or an areneferrocenium cation which is substituted or unsubstituted, optionally incorporated in a polymeric backbone, is advantageous insofar as it can be radicals which make it possible to initiate polymerization or crosslinking reactions or, generally, chemical reactions involving free radicals. Furthermore, this salt is readily soluble in polymer and monomer organic solvents, even of low polarity, in contrast to the derivatives of the anions of Cl$^-$ type commonly associated with the abovementioned cations. Furthermore, they exhibit a negligible vapor pressure, in contrast to the other radical initiators of peroxide or azo type, which is a considerable advantage in the processing of polymers as thin films, poor polymerization or crosslinking of the surface of the film being the consequence of the volatility of the initiator.

In an embodiment of the invention, $X_F$ is a perhalogenated alkyl radical preferably having from 1 to 12 carbon atoms or a perhalogenated alkylaryl radical preferably having from 6 to 9 carbon atoms. A heteroatom, such as O, N or S, can be present between two carbon atoms or at the end of the radical. Mention may be made, by way of examples, of the following compounds

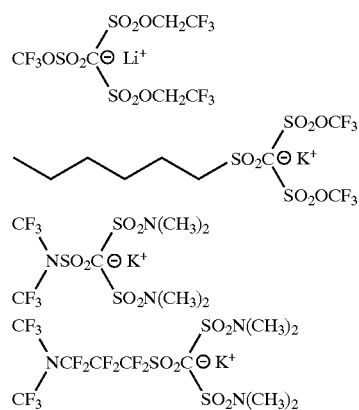

An $X_F$ substituent can also be a radical chosen from the group consisting of $R^HCF_2$—, $R^HCF_2CF_2$—, $R^HCF_2CF(CF_3)$— and $CF_3C(R^H)F$—, in which $R^H$ represents a nonperhalogenated organic radical.

An R, R' or $R^H$ substituent can be chosen from alkyl, alkenyl, oxa-alkyl, oxa-alkenyl, aza-alkyl, aza-alkenyl, thia-alkyl, thia-alkenyl and dialkylazo radicals having from 1 to 24 carbon atoms, or from aryl, arylalkyl, alkylaryl or alkenylaryl radicals having from 5 to 24 carbon atoms, it being possible for the said radicals optionally to be completely, or partially fluorinated, R and R' being other than a perfluoroalkyl when $X_FSO_x$ is a perfluoroalkylsufonyl. A few examples are given hereinbelow by way of illustration.

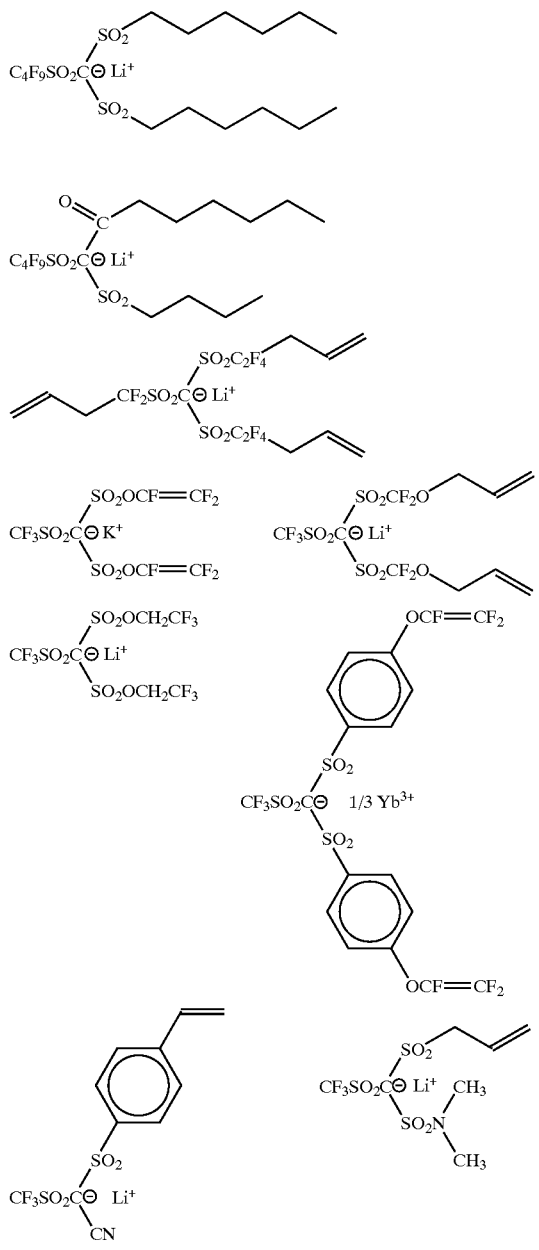

Two R and R' substituents can together form a divalent radical connected to a Y group and a Y' group. A compound example is given hereinbelow:

An R, R' or $R^H$ substituent can be chosen from alkyl or alkenyl radicals having from 1 to 12 carbon atoms and optionally comprising at least one O, N or S heteroatom in the main chain or in a side chain and/or optionally carrying a hydroxyl group, a carbonyl group, an amine group, an alkoxysilane group or a carboxyl group. When two substituents together form a divalent radical, this divalent radical can carry a heteroatom in a side chain and optionally form part of a ring. Mention may be made, by way of example, of

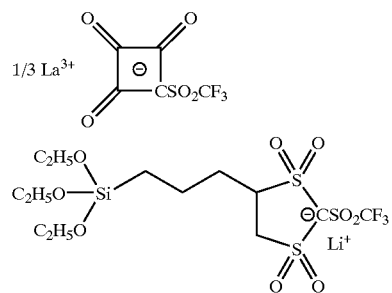

Two R and R' radicals can together form a biradical connected, at each of its ends, to an $-SO_2-C^--SO_2X_F$ anionic group. A polyionic compound is thus obtained, such as, for example:

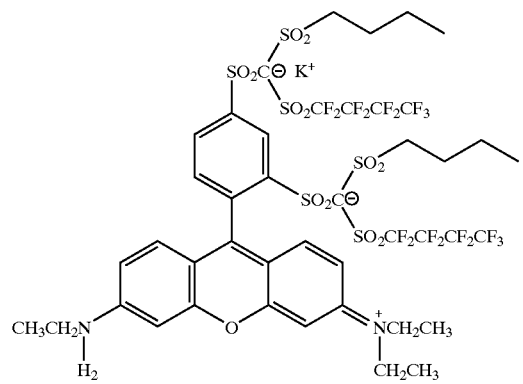

An R, R' or $R^H$ substituent can be a polymer radical, for example an oligo(oxyalkylene) radical. The salt of the composition of the invention is then provided in the form of a polymer carrying an $[(R'Y')(X_FSO_x)CY-]^-$ $M^+$ ionic group, where R is a polymer radical, or in the form of a polymer carrying an $[(RY)(R'Y')C-SO_x-]^-$ group, where $R^H$ is a polymer radical.

An R or R' substituent can be a repeat unit of a polymer. The salt of the composition of the invention is then provided in the form of a polymer in which at least a portion of the repeat units carry a side group to which is attached an $(X_FSO_x)CY-$, $M^+$ ionic group. Mention may be made, as an example, of a poly(oxyalkylene), a polyaniline or a poly(furan-vinylene), in which at least some oxyalkylene units carry an $[(R'Y')(X_FSO_x)CY-]^-$, $M^+$ or $[(RY)(R'Y')C-SO_x-]^-$ substituent. Mention may also be made of a polystyrene in which at least some styrene units carry an $[(R'Y')(X_FSO_x)CY-]^-$, $M^+$ substituent, for example a [styrenyl-$(R'Y')(X_FSO_x)CY-]^-$, $M^+$ substituent.

A specific category of salts, which salts can be used in a composition according to the invention, comprises the compounds in which an R, R' or $R^H$ substituent possesses at least one anionic ionophoric group and/or at least one cationic ionophoric group. The anionic group can, for example, be a carboxylate functional group ($-CO_2^-$), a sulfonate functional group ($-SO_3^-$) a disulfonimide functional group ($-SO_2NSO_2^-$) or a sulfonamide functional group ($-SO_2N=$). The cationic ionophoric group can, for example, be an iodonium, sulfonium, oxonium, ammonium, amidinium, guanidinium, pyridinium, imidazolium, imidazolinium, triazolium, phosphonium or carbonium group. The cationic ionophoric group can entirely or partially act as the M cation.

When an R, R' or $R^H$ substituent comprises at least one ethylenic unsaturated and/or one condensable group and/or one group dissociable by the thermal route, by the photochemical route or by ionic dissociation, the compounds of the invention are reactive compounds which can be subjected to polymerizations, crosslinkings or condensations, optionally with other monomers. They can also be used to attach ionophoric groups to polymers carrying the appropriate reactive functional group.

An R, R' or $R^H$ substituent can comprise a mesomorphic group or a chromophoric group or a self-doped electronic conducting polymer or a hydrolyzable alkoxysilane.

An R, R' or $R^H$ substituent can comprise a group capable of scavenging free radicals, for example a hindered phenol or a quinone.

An R, R' or $R^H$ substituent can also comprise a dissociating dipole, for example an amide functional group, a sulfonamide functional group or a nitrile functional group.

An R, R' or $R^H$ substituent can also comprise a redox couple, for example a disulfide group, a thioamide group, a ferrocene group, a phenothiazine group, a bis(dialkylaminoaryl) group, a nitroxide group or an aromatic imide group.

An R, R' or $R^H$ substituent can also comprise a complexing ligand.

An R, R' or $R^H$, RY or R'Y substituent can be an optically active group (for example an amino acid) or an optically or biologically active polypeptide.

When the anion of compound of the present invention corresponds to the formula $X_F-SO_x-C^--(Z)(Z')$ or $X_F-SO_x-C^--(Z)(YR)$, Z or Z' can be chosen from the group consisting of $-CN$, $-NO_2$, $-SCN$, $-N_3$, $-CF_3$, $R'_F CH_2-$ ($R'_F$ being a perfluorinated radical), $CF_2=CFO-$, $CF_2=CF-S-$, $CF_2=CF-$, $-C_2F_4H$, fluoroalkyloxy or perfluoroalkyloxy radicals, fluoroalkylthioxy radicals and perfluoroalkylthioxy radicals. Z or Z' can also be a radical comprising one or more aromatic nuclei optionally comprising at least one nitrogen, oxygen, sulfur or phosphorus atom, it being possible for the said nuclei optionally to be condensed nuclei and/or it being possible for the said nuclei optionally to carry at least one substituent chosen from the group consisting of halogens, $-OC_nF_{2n+1}$, $-OC_2F_4H$, $-SC_nF_{2n+1}$, $-SC_2F_4H$, $-O-CF=CF_2$, $-SCF=CF_2$, $-CN$, $-NO_2$, $-SCN$, $-N_3$, $-CF_3$, $CF_3CH_2-$, aza, thia and oxa radicals, perfluoroalkyl radicals, fluoroalkyloxy radicals, fluoroalkylthioxy radicals, alkyl, alkenyl, oxa-alkyl, oxa-alkenyl, aza-alkyl, aza-alkenyl, thia-alkyl or thia-alkenyl radicals, polymer radicals, and radicals possessing at least one cationic ionophoric group and/or at least one anionic ionophoric group;

it being understood that a Z or Z' substituent can be a monovalent radical, a portion of a multivalent radical connected to several $X_F-SO_xC^-<$ groups, or a segment of a polymer, and that two Z and Z' substituents can together form a multivalent group comprising a nucleus or several optionally condensed aromatic nuclei, including or not including the carbon carrying the anionic charge.

A Z substituent can also represent a repeat unit of a polymer. In this case, the ionic composition of the invention comprises a polymer in which at least some repeat units carry a $>CSO_2X_F$ ionic group. The Z substituent of an anionic group and the Z' substituent of a neighboring anionic group can also form a biradical. In this case, the ionic composition of the invention comprises a polymer in which the $C^-$ anionic center forms part of the backbone of the polymer, the $X_FSO_2$ group being found as a side substituent.

The solvent of the ionic composition of the invention can be an aprotic liquid solvent, a polar polymer or one of their mixtures.

The aprotic liquid solvent is chosen, for example, from linear ethers and cyclic ethers, esters, nitrites, nitro derivatives, amides, sulfones, sulfolanes, alkylsulfamides and partially halogenated hydrocarbons. The particularly preferred solvents are diethyl ether, dimethoxyethane, glyme, tetrahydrofuran, dioxane, dimethyltetrahydrofuran, methyl or ethyl formate, propylene or ethylene carbonate, alkyl carbonates (in particular dimethyl carbonate, diethyl carbonate and methyl propyl carbonate), butyrolactone, acetonitrile, benzonitrile, nitromethane, nitrobenzene, dimethylformamide, diethylformamide, N-alkylpyrrolidones (in particular N-methylpyrrolidone), dimethyl sulfone, tetramethylene sulfone and tetraalkylsulfonamides having from 5 to 10 carbon atoms.

An ionic composition of the invention can comprise a polar polymer solvent chosen from crosslinked or non-crosslinked solvating polymers carrying or not carrying grafted ionic groups. A solvating polymer is a polymer which comprises solvating units comprising at least one heteroatom chosen from sulfur, oxygen, nitrogen and fluorine. Mention may be made, as an example of solvating polymers, of polyethers with a linear, comb or block structure, forming or not forming a network, based on poly(ethylene oxide) or copolymers comprising the ethylene oxide or propylene oxide or allyl glycidyl ether unit, polyphosphazenes, crosslinked networks based on poly (ethylene glycol) crosslinked by isocyanates or networks obtained by polycondensation and carrying groups which make possible the incorporation of crosslinkable groups. Mention may also be made of block copolymers in which some blocks carry functional groups which have redox properties. Of course, the above list is not limiting and any polymer exhibiting solvating properties can be used.

An ionic composition of the present invention can simultaneously comprise an aprotic liquid solvent chosen from the abovementioned aprotic liquid solvents and a polar polymer solvent comprising units comprising at least one heteroatom chosen from sulfur, nitrogen, oxygen and fluorine. The composition can comprise from 2 to 98% of liquid solvent. Mention may be made, as example of such a polar polymer, of polymers which mainly comprise units derived from acrylonitrile, from vinylidene fluoride, from N-vinylpyrrolidone or from methyl methacrylate. The proportion of aprotic liquid in the solvent can vary from 2% (corresponding to a plasticized solvent) to 98% (corresponding to a gelled solvent).

An ionic composition of the present invention can additionally comprise a salt used conventionally in the prior art for the preparation of an ionically conducting material. Mention may be made, among the salts which can be added to an ionic composition according to the invention, of perfluoroalkanesulfonates, bis(perfluoroalkylsulfonyl) imides, bis(perfluoroalkylsulfonyl)methanes and tris (perfluoroalkylsulfonyl)methanes.

Of course, an ionic composition of the invention can additionally comprise the additives conventionally used in tonically conducting materials and in particular inorganic or organic fillers in the form of a powder or of fibers.

Generally, a compound $Q_1C(M)(Q_2)(Q_3)$ in which $Q_1$, $Q_2$ and $Q_3$ represent RY, R'Y', Z, Z' or $X_FSO_x$ can be prepared by the reaction of a compound possessing a leaving group L with a precursor of the final compound, according to the following reaction scheme:

L represents a leaving group such as F, Cl, Br, imidazolyl, triazolyl or $RSO_3$—. E represents an electrophilic group, such as M. For example, E can be H, Li, Na, K, a substituted or unsubstituted ammonium, MgL, $Si(R^7)_3$ or $Sn(R^8)_3$, $R^7$ and $R^8$ representing an alkyloxy radical.

A compound wherein the anion is $X_F$—$SO_x$—$C^-(Z)(Z')$ can be prepared by the reaction of a compound possessing a leaving group L with a precursor of the final compound, according to the following reaction scheme:

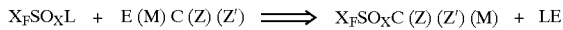

The compounds $EC(M)(Q^2)(Q^3)$ can be prepared by a similar method according to the reaction scheme

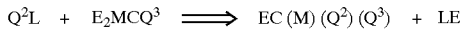

in which $Q^2$, $Q^3_1$, E, M and L have the meaning indicated above.

In an alternative form, where Q represents $X_FSO_x$—, the reaction can involve sulfur in the +2 or +4 oxidation state, according to the following reaction scheme:

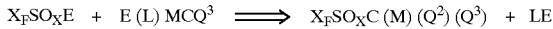

An ionic composition of the present invention of the polymer type can be prepared by dissolving the solvating polymer and an ionic compound carrying a $>CSO_xX_F$ group in a common solvent, such as acetonitrile, and then evaporating the solvent. The procedure can also be employed which consists in dissolving an ionic compound in a volatile solvent, in then dissolving this ionic composition and a solvating polymer in a common solvent and in evaporating the volatile solvent, the ionic composition being chosen so as to give a predetermined ionic compound/repeat unit ratio. An ionic composition of the present invention of the gell type can be obtained either by incorporating a liquid solvent in a polymer composition or by dissolving the ionic compound in a solvent in which the polymer can also be dissolved under warm conditions.

The salts of the ionic compositions of the present invention comprise at least one ionophoric group to which are attached substituents which can be highly varied. Bearing in mind the large choice possible for the substituents, the salts make it possible to induce properties of ionic conduction in the majority of organic media, liquids or polymers, possessing a polarity, even a low polarity. The applications are significant in the field of electrochemistry, in particular of the storage of energy in primary or secondary generators, in supercapacitors, in fuel cells and in electroluminescent diodes. When the composition according to the invention comprises a polymer salt (introduced directly into the composition or obtained in situ by polymerization of a monomer salt), it exhibits the properties listed above with the advantage of having an immobile anionic charge.

An ionic composition according to the invention can be used as electrolyte of an electrochemical device.

In this case, the salt is preferably chosen from the compounds for which the cation is ammonium or a cation derived from a metal, in particular of lithium or potassium, zinc, calcium or rare earth metals, or an organic cation, such as a substituted ammonium, an imidazolium, a triazolium, a pyridinium or a 4-(dimethylamino)pyridinium, the said cations optionally carrying a substituent on the carbon atoms of the ring. The electrolyte thus obtained exhibits a high conductivity and a high solubility in the solvents, due to the weak interactions between the positive charge and the negative charge. Its range of electrochemical stability is broad and it is stable in both reducing and oxidizing media. Mention may be made, among the salts which can be used in an ionic composition of the invention, of those which have an organic cation and a melting point of less than 150° C., in particular imidazolium, triazolium, pyridinium or 4-(dimethylamino)pyridinium salts. Mention may be made, by way of example, of the following salts:

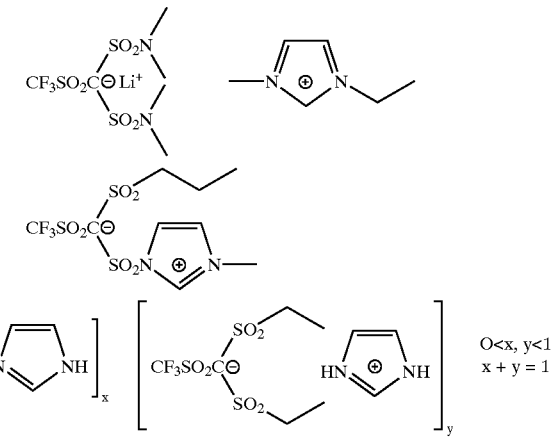

These salts exhibit a high intrinsic conductivity when they are in the molten phase. They can therefore be used with a minimum, indeed even zero, amount of solvent in forming an ionically conducting composition.

A composition of the invention in which the anion of the salt comprises a perhalogenated alkyl $X_F$ substituent having from 1 to 12 carbon atoms or a perhalogenated alkylaryl substituent having from 6 to 9 carbon atoms is particularly advantageous as electrolyte insofar as the weak interactions between the fluorine atoms of the chain result in high solubilities and a high conductivity, even in the case where the other substituents of the salt comprise groups having a tendency to give strong interactions, for example conjugated aromatic radicals or zwitterions.

A compound of the invention in which $X_F$ is chosen from the $R^HCF_2$—, $R^HCF_2CF_2$—, $R^HCF_2CF(CF_3)$— or $CF_3C(R^H)$ F— radicals makes it possible to very specifically adapt the properties of the tonically conducting material by appropriately choosing the $R^H$ substituent. In particular, it makes it possible to enjoy, with a reduced number of fluorine atoms, dissociation and solubility properties peculiar to the anionic charges of perfluorinated systems. These groups are readily accessible from industrial products, such as tetrafluoroethylene or tetrafluoropropylene. The reduced amount of fluorine renders these compound less sensitive to reduction by highly electropositive metals, such as aluminum, magnesium or, especially, lithium.

An ionic composition of the invention can be used as electrolyte in an electrochemical generator. Another subject-matter of the present invention is therefore an electrochemical generator comprising a negative electrode and a positive electrode separated by an electrolyte, characterized in that the electrolyte is an ionic composition as defined above. According to a specific embodiment, such a generator comprises a negative electrode composed of metallic lithium or of one of its alloys, optionally in the form of a nanometric dispersion in lithium oxide, or of a double lithium and transition metal nitride, or of an oxide of low potential having the general formula $Li_{1+y+x/3}Ti_{2-x/3}O_4$ ($0 \leq x \leq 1$, $0 \leq y \leq 1$), or of carbon and carbonaceous products resulting from the pyrolysis of organic matter. According to another embodiment, the generator comprises a positive electrode chosen from vanadium oxides $VO_x$ ($2 \leq x \leq 2.5$), $LiV_3O_8$, $Li_yNi_{1-x}CO_xO_2$, ($0 \leq x \leq 1$; $0 \leq y \leq 1$), manganese spinels $Li_yMn_{1-x}M_xO_2$ (M=Cr, Al, V, Ni, $0 \leq x \leq 0.5$; $0 \leq y \leq 2$), organic polydisulfides, FeS, $FeS_2$, iron sulfate $Fe_2(So_4)_3$, iron and lithium phosphates and phosphosilicates of olivine structure, or their products of substitution of the iron by manganese, used alone or as mixtures. The collector of the positive electrode is preferably made of aluminum.

Use will preferably be made, as electrolyte of an electrochemical generator, of an ionic composition comprising an alkali metal salt. Preference is very particularly given to lithium salts, optionally as a mixture with a potassium salt.

The salts in which the R and R' substituents represent an alkyl, an aryl, an alkylaryl or an aralkyl preferably having from 6 to 20 carbon atoms constitute good candidates for the ionic compositions intended to be used as electrolyte of an electrochemical generator. However, specific properties can be obtained by choosing other substituents. When the salt has at least one R, R' or $X_F$ substituent comprising a mesomorphic group or an ethylenic unsaturation and/or a condensable group and/or a group dissociable by the thermal route, by the photochemical route or by ionic dissociation, the ionic composition readily forms polymers or copolymers which are polyelectrolytes, either intrinsic, when the polymer carries solvating groups, or by addition of a polar solvent of liquid or polymer type or by mixing with such a solvent. These compositions of the polyelectrolyte type have a conductivity solely due to the cations.

When the salt of the ionic composition used as electrolyte carries at least one R, R' or $R^H$ substituent which is a self-doped electronic conducting polymer, the stability of the electrolyte is improved with respect to external agents and the conductivity is stable all the time, even at high temperatures. On contact with metals, such a composition gives very weak interfacial resistances. Its use as electrolyte makes it possible to protect from corrosion, in particular ferrous metals or aluminum, in particular when the aluminum is used as collector of the cathode of the generator. Mention may be made, by way of example, of:

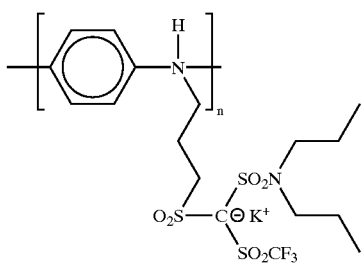

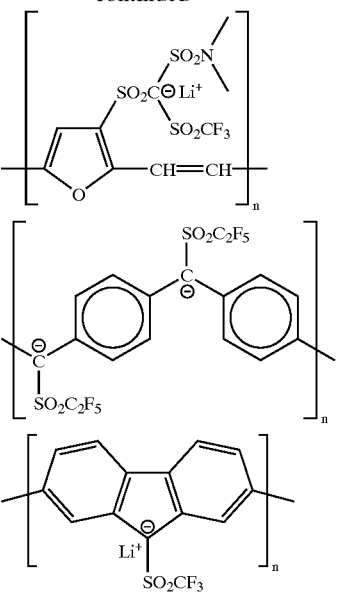

When the salt of the ionic composition used as electrolyte comprises an R, R' or $R^H$ substituent which comprises a redox couple (for example a disulfide, a thioamide, a ferrocene, a phenothiazine, a bis(dialkylaminoaryl) group, a nitroxide or an aromatic imide), the electrolyte has redox shuttle properties of use as charge equalization and protection component of the electrochemical generator.

The use of a salt carrying at least one R, R' or $R^H$ substituent which represents an alkyl, an aryl, an alkylaryl or an arylalkyl makes it possible to induce properties of mesogenic type in the electrolyte of the generator. Alkyls having from 6 to 20 carbon atoms or arylalkyl, in particular those comprising the biphenyl entity which form liquid crystal phases, are particularly preferred. The conduction properties of the nematic, cholesteric or discotic liquid crystal phases thus constituted are to reduce the mobility of the anions of the electrolyte, On particular in polymer electrolytes, without affecting the mobility of the cations. This distinctive feature is important for electrochemical generators involving lithium cations.

When a composition according to the invention is intended to be used as electrolyte of a lithium generator, the solvent is advantageously chosen from conventionally used polar aprotic liquid solvents. It can also be chosen from crosslinked or noncrosslinked solvating polar polymer solvents carrying or not carrying grafted ionic groups. Use may also be made, as solvent, of a gel obtained by mixing a liquid solvent and a polymer solvent. A poly(ethylene oxide) and a copolymer of ethylene oxide or of propylene oxide and of a crosslinkable monomer, such as allyl glycidyl ether and methyl glycidyl ether, are particularly advantageous.

An ionic composition of the invention can also be used for the preparation of the cathode of a lithium generator. The material of the cathode then comprises an ionic composition of the invention, in which the salt is an electronic conducting polymer. Mention may be made, by way of example of such a salt, of:

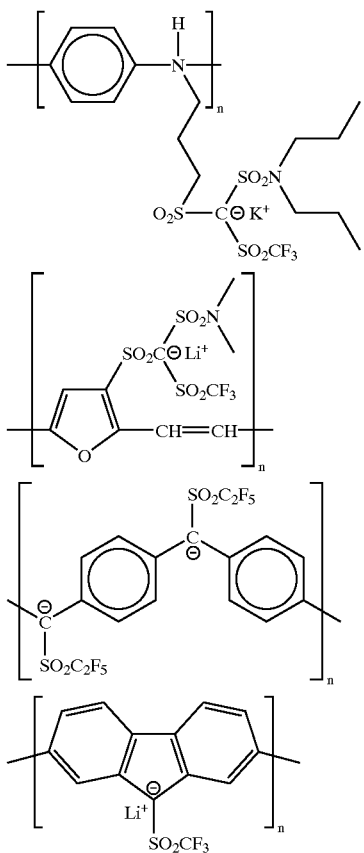

An ionic composition of the present invention can also be used as electrolyte of a supercapacitor. Another subject-matter of the present invention is consequently a supercapacitor using at least one carbon electrode with a high specific surface or one electrode comprising a redox polymer, in which the electrolyte is an ionic composition according to the present invention.

The cation of the salt of the ionic composition used as electrolyte of a supercapacitor is preferably an ammonium $NH_4^+$, a metal cation or an organic cation comprising a quaternized nitrogen atom. The preferred cations are Li, K, Ca, rare earths and the imidazolium, triazolium, pyridinium or 4-(dimethylamino)pyridinium ions.

The salt of the ionic composition of the invention used as electrolyte of a supercapacitor is advantageously chosen from the salts in which R, R' and $X_F$ have a low atom number, preferably of less than 3. The compounds in which R and R' represent —$CH_3$ or —$N(CH_3)_2$ and $X_F$ represents $CF_3$— are particularly preferred. It can be advantageous to add a small proportion of ionic compounds in which R and/or R' are long alkyl chains (n≧8) in order to act as surfactant and to improve the penetration of the liquid into the micropores of the carbon of the carbon electrode.

The solvents are preferably chosen from those which have a low viscosity and which confer a high conductivity to the composition, for example acetonitrile, alkyl carbonates, or the ethylene carbonate and dimethoxyethane mixture.

An ionic composition according to the present invention can be used as electrolyte of a fuel cell. For this specific application, the salt of the electrolyte is advantageously chosen from the $X_F$—$SO_x$—$C^-$—(Z)(Z') or $X_F$—$SO_x$—$C^-$(Z)(YR) salts, the first ones mentioned being preferred.

The cation of the compound used in the electrolyte of a fuel cell is preferably a hydronium, an ammonium, a metal cation or an organic cation comprising a quaternized nitrogen atom (as partial replacement for hydronium). The preferred cations are $H^+$, $H_3O^+$, $Li^+$, $K^+$, $Ca^{++}$ or the imidazolium, triazolium, pyridinium and 4-(dimethylamino)pyridinium ions.

The Z or Z' substituents of the ionic compound are preferably chosen from —$\Phi OC_nF_{2+1}$, —$\Phi OC_2F_4H$, —$\Phi SC_nF_{2n+1}$ and —$\Phi SC_2F_4H$, —$\Phi OCF=CF_2$, —$\Phi SCF=CF_2$, —$C_2F_4H$ and $CF_2=CF$—, n being an integer from 1 to 8. Such a salt is a precursor of stable monomers and polymers, in particular stable with respect to oxygen. The electrolyte thus exhibits high stability, even at temperatures of greater than 80° C., when the salt is a polymer.

An ionic composition of the present invention can be used as electrolyte in photoelectrochemical systems, in particular systems with conversion of light to electricity, and in systems for modulating light of electrochromic type. A photoelectrochemical device in which the electrolyte is an ionic composition according to the invention is another subject-matter of the present invention.

It is advantageous to use, as electrolyte, an ionic composition in which the cation of the salt is $H^+$, $H_3O^+$, $Na^+$, $K^+$, $NH_4^+$, an imidazolium, a triazolium, a pyridinium or a 4-(dimethylamino)pyridinium. When the electrophotochemical device is a system for converting light to electricity or a system for modulating light of the electrochromic type, it is advantageous to use, in the electrolyte, a salt which carries at least one R, R' or $R^H$ substituent comprising a redox couple, such as a disulfide, a thioamide, a ferrocene, a phenothiazine, a bis(dialkylaminoaryl) group, a nitroxide or an aromatic imide. The electrolyte thus exhibits redox shuttle properties of use in ensuring the passage of current without polarization. When the cation of the ionic compound is an imidazolium, a triazolium, a pyridinium or a 4-(dimethylamino)pyridinium, the ionic compound is molten at room temperature and exhibits a high ionic conductivity of greater than $10^{-3}$ S.$cm^{-1}$. A composition comprising the said salt, the corresponding base (imidazole, triazole, pyridine or 4-(dimethylamino)pyridine) and a poly(ethylene oxide), preferably of high mass or crosslinkable, constitutes an anhydrous protonic conducting polymer.

For an electrochromic device comprising dyes, use is made, as electrolyte, of a composition according to the invention in which the salt is a compound having molten salt properties and which additionally comprises supplementary dyes which change color on passing from the oxidized state to the reduced state and vice versa.

An ionic composition according to the invention can also be used as electroactive dye or electrolyte in a device for optical display. In this specific use, it is advantageous to choose, for R, R' or $R^H$, an alkyl, an aryl, an alkylaryl or an arylalkyl which makes it possible to induce properties of mesogenic type in the ionic composition. Alkyl groups having from 6 to 20 carbon atoms or arylalkyl groups in particular those comprising the biphenyl entity which form liquid crystal phases, are particularly preferred.

An ionic composition of the present invention can also be used for the p or n doping of an electronically conducting polymer and this use constitutes another subject-matter of the present invention. The anions of the salt of the ionic composition of the invention can act as countercharge to polycationic conjugated polymers, such as polyacetylene, polypyrrole, polythiophene, polyparaphenylene, polyquinolines and their alternating copolymers with acetylene (ex. polyparaphenylenevinylene) and their derivatives of substitution by alkyl, alkoxy or aryl groups and the like. Optionally, the polymerization or the doping are carried out by the electrochemical route starting from the ionic compositions or by exchange of the anions of an already doped polymer by the anions of the ionic compositions.

The anionic charge carried by one of the $X_F$—$SO_x$—$C^-$(Z)(Z')$, $X_F$—$SO_x$—$C^-$(YR)(Y'R')$ or $X_F$—$SO_x$—$C^-$(Z)(YR) anions exerts a stabilizing effect on the electronic conductors of conjugated polymer type and the use of a composition comprising a salt carrying at least one Z, Z', R or R' substituent comprising a long alkyl chain makes it possible to render these polymers soluble in the usual organic solvents, even in the doped state. The grafting of these charges to the polymer itself gives polymers, the overall charge of which is cationic, which are soluble in organic solvents and which exhibit, in addition to their stability, corrosion-resistant properties with respect to metals, aluminum and ferrous metals. Another subject-matter of the present invention is electronically conducting materials comprising an ionic composition of the present invention in which the cationic part of the salt is a polycation composed of a "p"-doped conjugated polymer. The preferred salts for this application are those in which one of the Z, Z', R or R' substituents comprises at least one alkyl chain having from 6 to 20 carbon atoms. Mention may be made, by way of example, of the compounds in which R or R' is an alkyl radical. Mention may be also be made of the compounds in which $X_F$ is $R^HCF_2$—, $R^HCF_2CF_2$—, $R^HCF_2CF(CF_3)$— or $CF_3C(R_H)F$—, in which compounds $R^H$— represents an alkyl radical. Mention may additionally be made of the compounds in which Z represents an aromatic nucleus carrying an alkyl radical.

It has been observed that the strong dissociation of the ionic species of the compounds of the invention is reflected by stabilization of the carbocations, in particular of those in which there exists conjugation with oxygen or nitrogen and, surprisingly, by a high activity of the protonated form of the compounds of the invention with regard to some monomers. Another subject-matter of the present invention is therefore the use of an ionic composition as photochemical or thermochemical initiator source of Brönsted acid catalyst of polymerization or of crosslinking of monomers or of prepolymers capable of reacting by the cationic route, as catalyst for various chemical reactions or as catalyst for the modification of polymers. Preference is very particularly given, as catalyst for the chemical modification of polymers, to the compositions in which the cation of the salt is a proton, an oxonium, Li, Mg, Cu, a rare earth, trimethylsilyl, a ferrocene, a zirconocene or a zirconoindocene.

The process for the polymerization or for the crosslinking of monomers or of prepolymers capable of reacting by the cationic route is characterized in that use is made of an ionic composition of the invention as photoinitiator, source of acid catalyzing the polymerization reaction. The ionic compositions according to the invention in which the cation of the salt is a group possessing an ~N=N$^+$ or —N=N— linkage, a sulfonium group, an iodonium group or an areneferrocenium cation which is substituted or unsubstituted, optionally incorporated in a polymeric backbone, are preferred. The compositions comprising a 2,2'[Azobis(2-2'-imidazolinio-2-yl)propane]$^{2+}$ or 2,2'-Azobis(2-amidiniopropane)$^{2+}$ salt are particularly suited as photothermal initiators. The compositions comprising an iodonium salt are particularly suited as photochemical initiator. Mention may be made, by way of example of salts, of:

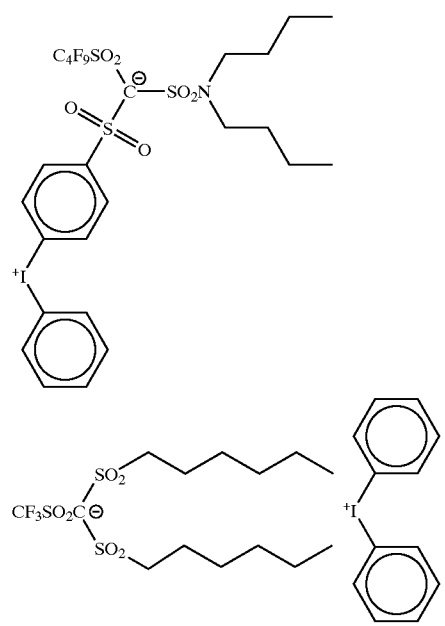

The choice of the $X_F$ substituent, on the one hand, and of the R, R' or Z substituents, on the other hand, is made so as to enhance the compatibility of the salt with the solvents used for the reaction of the monomers or of the prepolymers and according to the properties desired for the final polymer. For example, the choice of unsubstituted alkyl radicals provides solubility in not very polar media. The choice of radicals comprising an oxa group or a sulfone will provide solubility in polar media. The radicals including a sulfoxide group, a sulfone group, a phosphine oxide group or a phosphonate group, obtained respectively by addition of oxygen to sulfur or phosphorus atoms, can confer, on the polymer obtained, improved properties as regards adhesion, gloss or resistance to oxidation or to UV radiation. The monomers and the prepolymers which can be polymerized or crosslinked using the photoinitiators of the present invention are those which can be subjected to cationic polymerization.

Mention may be made, among the monomers, of monomers which comprise a cyclic ether functional group, a cyclic thioether functional group or a cyclic amine functional group, vinyl compounds (more particularly vinyl ethers), oxazolines, lactones and lactams.

Mention may be made, among the prepolymers, of the compounds in which epoxy groups are carried by an aliphatic chain, an aromatic chain or a heterocyclic chain, for example glycidic ethers of bisphenol A ethoxylated by 3 to 15 ethylene oxide units, siloxanes possessing side groups of the epoxycyclohexene-ethyl type which are obtained by hydrosilylation of copolymers of dialkyl-, alkylaryl- or diarylsiloxane with methylhydrosiloxane in the presence of vinylcyclohexene oxide, condensation products of the sol-gel type obtained from triethoxy- or trimethoxysilapropyl-cyclohexene oxide, or urethanes incorporating the reaction products of butanediol monovinyl ether and of an alcohol with a functionality of greater than or equal to 2 with an aliphatic or aromatic di- or triisocyanate.

The polymerization process according to the invention consists in mixing at least one monomer or prepolymer capable of polymerizing by the cationic route and at least one ionic composition of the invention and in subjecting the mixture obtained to actinic radiation or β radiation. The reaction mixture is preferably subjected to the radiation after having been put into the form of a thin layer having a thickness of less than 5 mm, preferably into the form of a thin film having a thickness of less than or equal to 500 μm. The duration of the reaction depends on the thickness of the sample and on the power of the source at the active wavelength λ. It is defined by the rate of forward progression past the source, which is between 300 m/min and 1 cm/min. Layers of final material having a thickness of greater than 5 mm can be obtained by repeating the operation several times, which operation consists in spreading a layer and in treating it with the radiation.

The amount of composition acting as photochemical initiator used is generally between 0.01 and 15% by weight with respect to the weight of monomer or of prepolymer, preferably between 0.1 and 10% by weight.

An ionic composition of the present invention comprising a very low, indeed even zero, amount of solvent can be used as photochemical initiator, in particular when it is desired to polymerize liquid monomers in which the salt of the ionic composition used as photochemical initiator is soluble or readily dispersible. This form of use is particularly advantageous because it makes it possible to eliminate the problems related to solvents (toxicity, inflammability).

An ionic composition of the present invention can also be used as photochemical or thermochemical initiator in the form of a homogeneous solution in a solvent which is inert with respect to polymerization, which solution is ready for use and readily dispersible, in particular in the case where the medium to be polymerized or to be crosslinked exhibits a high viscosity.

Mention may be made, as example of inert solvent, of volatile solvents, such as acetone, methyl ethyl ketone and acetonitrile. Mention may also be made of nonvolatile solvents, such as, for example, propylene carbonate, γ-butyrolactone, ether-esters of mono-, di- or triethylene or -propylene glycols, ether-alcohols of mono-, di- or triethylene or -propylene glycols, diethers of mono-, ,di- or triethylene glycol and diethers of mono-, di- or tripropylene glycol, and plasticizers, such as esters of phthalic acid or of citric acid.

In order to irradiate the reaction mixture, the radiation can be chosen from ultraviolet radiation, visible radiation, X-rays, γ-rays and β radiation. When ultraviolet light is used as actinic radiation, it can be advantageous to add, to the photochemical or thermochemical initiators of the invention, photosensitizers intended to make possible efficient photolysis with less energetic wavelengths than those corresponding to the absorption maximum of the photochemical or thermochemical initiator, such as those emitted by industrial devices (λ≈300 nm for mercury vapor lamps, in particular).

Among the various types of radiation mentioned, ultraviolet radiation is particularly preferred. On the one hand, its use is more convenient than the use of the other types of radiation mentioned. On the other hand, the photochemical initiators are generally directly sensitive to UV rays and the photosensitizers become increasingly efficient as the difference in energy (δλ) decreases.

The ionic compounds of the invention can also be employed in combination with initiators of radical type which are generated thermally or by the action of actinic radiation. It is thus possible to polymerize or to crosslink mixtures of monomers or of prepolymers comprising functional groups with different modes of polymerization, for example monomers or prepolymers polymerizing by the radical route and monomers or prepolymers polymerizing by the cationic route. This possibility is particularly advantageous in creating interpenetrating networks having physical properties different from those which would be obtained by simple mixing of the polymers resulting from the corresponding monomers.

Another subject-matter of the invention is the use of the ionic compositions of the invention in reactions for the chemical amplification of photoresists for microlithography. During such a use, a film of a material comprising a polymer and an ionic composition of the invention is subjected to irradiation. The irradiation leads to the formation of the acid by replacement of the cation M by a proton, which catalyzes the decomposition or the conversion of the polymer. After decomposition or conversion of the polymer on the parts of the film which have been irradiated, the monomers formed or the converted polymer are removed and there remains an image of the unexposed parts. For this specific application, it is advantageous to use a composition of the invention which is provided in the form of a polymer comprised essentially of styrenyl repeat units carrying an $X_F$—$SO_x$—$C^-$ ionic substituent in which the cationic part is an iodonium or a sulfonium. These compounds make it possible to obtain, after photolysis, products which are not volatile and therefore neither corrosive nor odorous when sulfides are produced from the decomposition of the sulfonium. Mention may in particular be made, among polymers which can thus be modified in the presence of a compound of the invention, of polymers comprising ester units or aryl tert-alkyl ether units, for example poly(phthalaldehydes), polymers of bisphenol A and of a diacid, poly(tert-butoxycarbonyloxystyrene), poly(tert-butoxy-α-methylstyrene), poly(di-tert-butyl fumarate-co-allyltrimethylsilane) and polyacrylates of a tertiary alcohol, in particular poly(tert-butyl acrylate). Other polymers are described in J. V. Crivello et al., Chemistry of Materials, 8, 376–381 (1996).

In the salts of the compositions of the present invention, the ion pairs exhibit a very strong dissociation, which makes possible the expression of the intrinsic catalytic properties of the $M^{m+}$ cation, the active orbitals of which are readily exposed to the substrates of the reaction, in various media. The majority of the important reactions of organic chemistry can thus be carried out under conditions which are not very restrictive, with excellent yields and the ability to separate the catalyst from the reaction mixture. The demonstration of asymmetric induction by the use of an ionic composition according to the invention comprising a salt which carries a chiral group is particularly significant because of its generality and its ease of implementation. It should be noted that chiralperfluorinated molecules $[(R_FSO_2)_3C]^-1/mM^{m+}$ are unknown and would only exhibit a negligible optical activity, due to the low polarizability of the perfluorinated groups. Another subject-matter of the present invention is consequently the use of the compositions of the invention as catalysts in Friedel-Crafts reactions, Diels-Alder reactions, aldol reactions, Michael additions, allylation reactions, pinacol coupling reactions, glycosylation reactions, ring opening reactions of oxetanes, methathesis reactions of alkenes, polymerizations of Ziegler-Natta type, polymerizations of the methathesis type by ring opening and polymerizations of the methathesis type of acyclic dienes. The preferred ionic compositions of the invention for use as catalyst for the above reactions are those in which the cation of the salt is chosen from H, lithium, magnesium, transition metals in the divalent or trivalent state, rare earths, platinoids and their organometallic couples, in particular metallocenes. Compositions comprising a salt having an optically active R, R' or Z substituent are particularly effective in enantioselective catalysis.

The compositions of the invention can also be used as solvent for carrying out chemical, photochemical, electrochemical or photoelectrochemical reactions. For this specific use, preference is given to the ionic compositions in which the salt has a cation of the imidazolium, triazolium, pyridinium or 4-(dimethylamino)pyridinium type, the said cation optionally carrying a substituent on the carbon atoms of the ring, and an anion in which the substituents have a low number of carbon atoms, preferably of less than or equal to 4. Preference is very especially given, among these salts, to those which have a melting point of less than 150° C., more particularly of less than 100° C. The amount of solvent can then be minimized. Use may also be made of a composition comprising a salt of a solvated metal cation, for example solvated by a polyethylene glycol preferably having a mass of less than 1000.

Dyes of cationic type (cyanines) are increasingly frequently used as sensitizers for photographic films, for the optical storage of information (write-accessible optical disks) or for lasers. The tendency of these conjugated molecules to stack together when they are in solid phases limits their use, as a result of variations in the optical properties in comparison with the isolated molecule. The use of ionic compositions of the invention for the manufacture of cationic dyes, the counterions of which, optionally attached to this same molecule, correspond to the functionalities of the invention, makes it possible to reduce the phenomena of aggregation, including in polymer solid matrices, and to stabilize these dyes. Another subject-matter of the present invention is the use of an ionic composition according to the invention as cationic dye composition. The particularly preferred ionic compositions for this application are those which comprise a salt in which the negative charge or charges of the $X_F$—$SO_x$—$C^-(Z)(Z')$, $X_F$—$SO_x$—$C^-(YR)(Y'R')$ or $X_F$—$SO_x$—$C^-(Z)(YR)$ anionic group are either attached to the dye molecule or constitute the counterion of the positive charges of the dye. Mention may be made, by way of example of such compounds, of the following compounds:

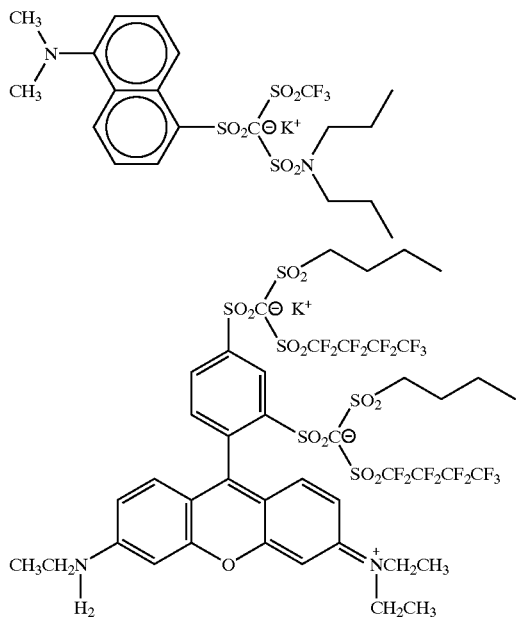

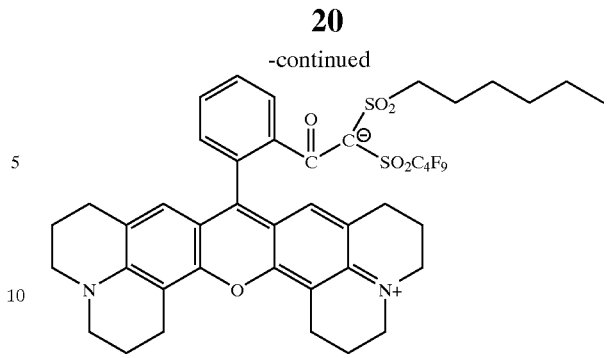

The present invention is described in more detail by the following examples, to which it is not, however, limited.

EXAMPLE 1

100 mmol of bis(chlorosulfonyl)methane $(ClSO_2)_2CH_2$, prepared according to the method of Fild and Rieck (Chem. Ztg., 100, 1976, 391), were slowly added to 200 ml of a 5M dimethylamine solution. After stirring for two hours, the water was evaporated and the residue was taken up in ether. After evaporating the ether, the bis(dimethylaminosulfonyl)methane $((CH_3)_2NSO_2)_2CH_2$ was purified by sublimation. 20 mmol of $((CH_3)_2NSO_2)_2CH_2$ and 20 mmol of sodium hydride, portionwise, were then added to 20 ml of tetrahydrofuran. After one hour, 20 mmol of trifluoromethanesulfonylimidazole (sold by Fluka) were added. After stirring for 24 hours, the solvent was evaporated, the residue was then taken up in ethanol and 25 mmol of $K_2CO_3$ were added. After filtering and evaporating the suspension, the potassium salt $[(CH_3)_2NSO_2]_2C(K)SO_2CF_3$ was recrystallized from water. This salt was subsequently treated with a stoichiometric amount of lithium chloride in tetrahydrofuran. The corresponding lithium salt was thus obtained:

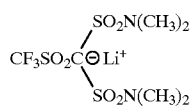

This salt exhibits excellent solubility in the usual organic solvents (tetrahydrofuran, acetonitrile, dimethylformamide, ethyl acetate, glymes, and the like) and in aprotic solvating polymers, such as poly(ethylene oxide). A solution of the salt in poly(ethylene oxide) at a concentration O/Li=12/1 exhibits an ionic conductivity of greater than $10^{-4}$ S.cm$^{-1}$ at 60° C. A concentrated solution of this salt in acetone can be used for the catalysis of Diels-Alder reactions.

A generator according to the lithium-polymer technology was prepared by using an anode made of metallic lithium, an electrolyte composed of an ethylene oxide, allyl glycidyl ether and methyl glycidyl ether terpolymer comprising this lithium salt at a concentration O/Li=20/1 and a composite cathode based on vanadium oxide (40% by volume), on carbon black (5% by volume) and on an electrolyte identical to that described above (50% by volume). This generator gave a cycling profile at 60° C. equivalent to that obtained by using lithium bis(trifluoromethane-sulfonyl)imide (LiTFSI), which is one of the commonest salts in this application.

EXAMPLE 2

20 mmol of potassium triflinate $CF_3SO_2K$ (sold by Parish Chemicals, Utah, USA) and 20 mmol of 4-bromo-1-bromomethylenebenzene $BrCH_2C_6H_4Br$ were added to 20 ml of anhydrous tetrahydrofuran. After stirring for 24 hours, a potassium bromide precipitate was formed, which precipitate was removed by filtration. 40 mmol of sodium hydride NaH were then added portionwise, followed, after stirring for one hour, by a catalyst tetrakis(triphenylphosphine)$Pd^0$ (2 mol %). The reaction mixture was then stirred for 48 hours and then precipitated from a saturated aqueous potassium chloride solution. The following product was then obtained:

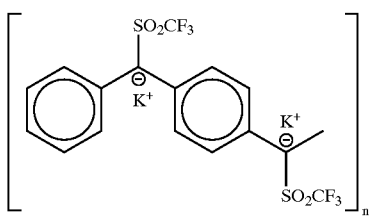

10 mmol of the polymer obtained were subsequently doped by treatment with 2.5 mmol of diacetatoiodosobenzene $(CH_3CO_2)_2IC_6H_5$ (sold by Lancaster) in 10 ml of dimethylformamide. After filtering and evaporating the solvent, an electronically conducting polymer (ECP) with anionic doping was obtained exhibiting a conductivity of the order of 6 $S.cm^{-1}$, determined by a four point measurement. This conductivity exhibits good stability in a wet medium.

The polymer compound of the present example is a good inhibitor of corrosion of aluminum and ferrous metals in acidic or chloride medium. The treatment of the surfaces to be protected is carried out simply by deposition of a solution of the ECP in a mixture of water and dimethylformamide, in the form of a paint, and then drying and a heat treatment at 100° C. This polymer compound has also made it possible to obtain adherent conducting coatings, the conductivity of which is stable in air, on plastics treated by the Corona effect.

The polymer ionic compound of the present example can also be used for the preparation of the cathode of a battery. The cathode is a composite cathode comprising the polymer salt obtained in the present example (40% by volume) and a poly(ethylene oxide) with a mass of $3 \times 10^5$. The electrolyte is a poly(ethylene oxide) film with a mass of $5 \times 10^6$ comprising the lithium salt of bis(trifluoromethanesulfonyl) imide at a concentration O/Li=20/1. The anode is metallic lithium. After having assembled the combination in a button cell case, this battery was cycled at a temperature of 60° C. between 2 V and 3.9 V. More than 500 charging/discharging cycles could be carried out while retaining 70% of the capacity of the first cycle.

EXAMPLE 3

20 mmol of potassium triflinate $CF_3SO_2K$ and 20 mmol of 1-dimethylaminosulfonyl-1-bromomethane $Me_2NSO_2CH_2Br$, prepared from $ClSO_2CH_2Br$ (sold by Lancaster), were added to 20 ml of anhydrous pyridine. After stirring for 24 hours, the pyridine was evaporated and the residue was taken up in 30 ml of a 4M hydrochloric acid solution. The aqueous phase was subsequently extracted with ether, the extract was dried over magnesium sulfate, the ether was then evaporated and the residue was sublimed.

The compound $Me_2NSO_2CH_2SO_2CF_3$ was thus recovered. This compound was stirred in the presence of potassium phosphate $K_3PO_4$ in tetrahydrofuran for 24 hours. After filtering and evaporating the solvent, the potassium salt of $Me_2NSO_2CH_2SO_2CF_3$ was then obtained. 10 mmol of this potassium salt were introduced into 15 ml of tetrahydrofuran, followed by 10 mmol of styrenesulfonyl chloride (sold by Monomer-Polymer & Dajac Laboratories). After 24 hours, 10 mmol of lithium chloride were added and then the reaction mixture was stirred for 6 hours. After filtering and evaporating the solvent, the following product was obtained:

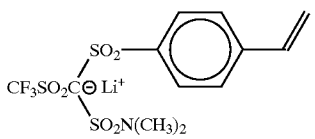

6 mmol of this salt, 4 mmol of acrylonitrile and 100 μmol of 1,1'-azobis(cyclohexanecarbonitrile) were dissolved in 20 ml of anhydrous tetrahydrofuran and degassing was carried out by flushing with dry argon. The acrylonitrile was then copolymerized with the styrene derivative under argon by heating the reaction mixture at 60° C. for 48 hours. After cooling, the solution was concentrated and then the polymer was recovered by reprecipitating from ether. The following copolymer was thus obtained:

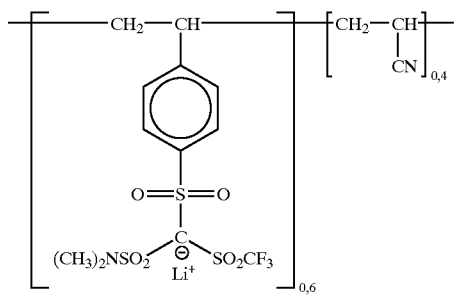

Ethylene carbonate (EC) and propylene carbonate (PC) were introduced into this copolymer in the following proportions, expressed as percentage by weight: copolymer 30%, EC 35% and PC 35%, and a polyelectrolyte was obtained in the form of a gel. This gel exhibits good mechanical properties and a conductivity of greater than $10^{-4}$ $S.cm^{-1}$ at 30° C. The cationic transport number in this electrolyte is 0.85.

An electrochemical generator was assembled by using, as anode, a carbon coke (80% by volume) mixed with the copolymer of the present example (20% by volume). The electrolyte is the gel copolymer described above. The cathode is a composite cathode comprising carbon black (6% by volume), $LiNiO_2$ (75% by volume) and the copolymer of the present example (20% by volume). This generator gave good performances on cycling at 25° C. After 500 charging/discharging cycles between 3 and 4.2 V, a capacity of greater than 75% of the capacity of the first cycle was observed. In addition, the generator exhibits very good performances during taking up of power, due to the use of fixed anions, which also improved the change in the interfacial resistance.

Following an equivalent process, a polyanion was also synthesized comprising 3 mol % of the lithium salt and 97 mol % of acrylonitrile. This copolymer made it possible to induce antistatic properties in polyacrylonitrile fibers.

EXAMPLE 4

40 mmol of potassium hydride were slowly added, under argon, to a solution of 20 mmol of 1,3-dithiolane-1,1,3,3-tetraoxide (prepared according to the Gibson method: J. Chem. Soc., 1930, 12) in 20 ml of anhydrous tetrahydrofuran. After stirring for one hour, 30 mmol of trifluoromethanesulfonyl fluoride (sold by Apollo, United Kingdom) were bubbled through over a period of one hour. After stirring for 24 hours, the reaction mixture was filtered, the solvent evaporated and the residue dried. The following potassium salt was thus obtained:

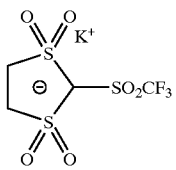

10 mmol of this potassium salt were dissolved in 10 ml of anhydrous tetrahydrofuran. 10 mmol of lithium hydride were then added under argon and portionwise, followed by 10 mmol of (chloropropyl)triethoxysilane (sold by Fluka). After 24 hours, the reaction mixture was filtered, in order to remove the potassium chloride precipitate formed, and then the solvent was evaporated. The following product was thus obtained:

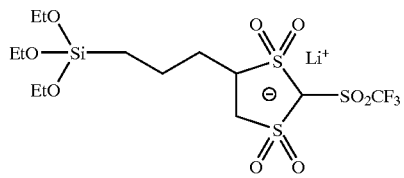

A solution of this lithium salt with O-[2-(trimethoxysilyl) ethyl]—O'-methylpolyethylene glycol with a mass of 5000 (sold by Shearwaters Polymers)(3:1 in moles) was prepared in a water/methanol mixture. A glass plate, etched with nitric acid and then dried at 100° C., was subsequently dipped in the solution for a few minutes. After rinsing with methanol and drying, a surface conductivity of $3 \times 10^{-5}$ S(square) was measured, sufficient to give antistatic properties to the surface of the glass.

EXAMPLE 5

By proceeding as in Example 1, but replacing dimethylamine by dibutylamine, the potassium salt $[(C_4H_9)_2NSO_2]_2CKSO_2CF_3$ was prepared. 5 mmol of this potassium salt and 5 mmol of diphenyliodonium chloride $(C_6H_5)_2ICl$ were subsequently stirred together for 24 hours in water. After extracting the aqueous phase with dichloromethane, evaporating the dichloromethane and drying, the following product was recovered:

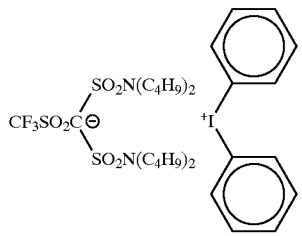

This salt makes it possible to initiate, under the effect of actinic radiation (light, γ-rays or electron beams), the cationic crosslinking reaction of electron-rich monomers (vinyl ethers, alkyl vinyl ethers, and the like) It is soluble in the majority of the usual organic solvents (tetrahydrofuran, acetonitrile, dimethylformamide, ethyl acetate, glymes, and the like) and in aprotic solvating polymers, such as poly (ethylene oxide) . It is also soluble to more than 10% by weight in reactive solvents, such as triethylene glycol divinyl ether, in contrast, for example, to the bis (trifluoromethanesulfonyl)imide salt of diphenyliodonium. This salt was used as photochemical initiator in the polymerization of triethylene glycol divinyl ether. 1% by weight of the salt was dissolved in the triethylene glycol divinyl ether and the irradiation was carried out with U.V. radiation at 254 nm with a power of 1900 mW/cm². After a few seconds, the reactive solvent set solid, the reaction being highly exothermic.

EXAMPLE 6

50 mmol of the potassium salt $((CH_3)_2NSO_2)_2CKSO_2CF_3$, prepared according to the procedure of Example 1, were coground in an agate mortar in a glove box with 17.27 g (150 mmol) of ammonium hydrogensulfate $HSO_4NH_4$ (sold by Aldrich) . The acidic form $[(CH_3)_2NSO_2]_2CHSO_2CF_3$ was recovered by sublimation under ultrahigh vacuum at 80° C.

20 mmol of $[(CH_3)_2NSO_2]_2CHSO_2CF_3$ were added to a solution of 20 mmol of imidazole in 15 ml of ether and then, after stirring for 24 hours, evaporating the ether and drying, the imidazolium salt was obtained:

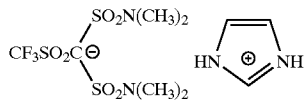

Grinding, in a glove box, a mixture of imidazole and of the imidazolium salt in a 1/2 molar ratio made it possible to obtain a composition having a melting temperature below room temperature. This molten salt exhibits a high protonic conductivity of greater than $10^{-3}$ S.cm$^{-1}$ at 60° C. The addition to the molten salt of poly(ethylene oxide), preferably of high mass or which can subsequently be crosslinked, makes it possible to obtain an anhydrous protonic conducting polymer electrolyte, without loss of conductivity.

Such a polymer electrolyte is particularly advantageous in the preparation of systems for modulating light, such as electrochromic glazings or electrochromic systems comprising dyes. A membrane which is optically transparent in the visible region and which has a good mechanical behavior was thus obtained by using a polymer electrolyte composed of 80% by weight of the above molten salt and of 20% by weight of poly(ethylene oxide) with a mass $M_w = 5 \times 10^6$. An electrochromic system was subsequently prepared, in a glove box, using this electrolyte confined between a first electrode, composed of the deposition on a glass plate of a layer of hydrogenated iridium oxide $H_xIrO_2$ and of a conducting sublayer of tin oxide, and a second electrode, composed of a layer of tungsten trioxide $WO_3$ and of a conducting sublayer of tin oxide. This electrochromic system makes possible a variation in the optical absorption varying from 80% (decolored state) to 30% (colored state) and good performances in cycling. More than 20,000 coloration/decoloration cycles were carried out.

An electrochromic system was also prepared by dissolving two complementary dyes in the molten salt described above. 1.62 g (5 mmol) of the imidazolium salt of (trifluoromethanesulfonyl)[bis(dimethylaminosulfonyl)] methide were coground in a glove box with 1.02 g of imidazole (15 mmol). 16.5 mg (50 μmol) of the leuco form of malachite green (colorless reduced state) and 29.5 mg (50 μmol) of the 3-(4,5-dimethylthiazolyl-2-yl)-2,5-diphenyl-2H-tetrazolium (MTT) salt of trifluoromethanesulfonyl (dimethylaminosulfonyl)imide (colorless oxidized state, obtained by ionic exchange in water from the bromide) were then added. 5% by weight of poly(ethylene oxide) with a mass $M_w=3\times10^5$ were then added. The gel obtained was deposited between two glass plates covered with a conducting layer of tin oxide ($SnO_2$). After pressing under vacuum, in order to homogenize the coating, and sealing, in order to render it leaktight, an electrochromic system comprising dyes was obtained. A potential of 1300 mV was applied to the system using a potentiostat. The system then became colored, the oxidized form of the malachite green and the reduced form of the MTT each exhibiting an intense absorption band in the visible region. By applying a potential of −500 mV, a relatively fast decoloration of the system was observed (less than 60 s). Such an electrochromic system is easy to employ, even for large devices (greater than one m²) which use both glass and a suitably treated polymer as conducting transparent electrode. Furthermore, the energy necessary to retain the coloration is relatively low, less than 1 W/m².

EXAMPLE 7

20 mmol of the potassium salt (($CH_3$)$_2NSO_2$)$_2$$CKSO_2CF_3$, prepared according to the procedure of Example 1, and 22 mmol of 1-ethyl-3-methyl-1-H-imidazolium chloride (10% excess, sold by Aldrich) were mixed in water. A denser liquid phase than the water was obtained and was recovered by extraction with dichloromethane. After evaporating the dichloromethane and drying the liquid obtained under vacuum at 40° C., the following molten salt was obtained:

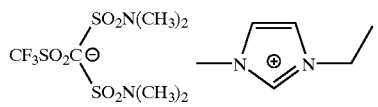

This molten salt exhibits a conductivity of greater than $10^{-3}$ S.cm$^{-1}$ and a freezing point of less than 25° C. Its broad range of redox stability makes it particularly advantageous electrolyte in electrochemical generators, such as lithium batteries, supercapacitors, systems for modulating light or photovoltaic cells.

An electrochemical photovoltaic cell similar in principle to that disclosed in European Patent EP 613,466 was prepared by assembling a system composed of two electrodes separated by an empty space with a thickness of 30 μm. The first electrode was coated with a layer of nanoparticles of titanium dioxide $TiO_2$ with a thickness of 0.25 μm, on which layer was adsorbed 1,3-phenylsulfonyl (trifluoromethanesulfonyl-dimethyl-aminosulfonyl)methane rhodamine B as sensitizer. The space between the electrodes was filled with an electrolyte composed of the molten salt into which had been introduced 10% by weight of methyl-hexylimidazolium iodide and 10 mmol of iodine. This photovoltaic cell gave advantageous performances, in particular a short circuit current of 103 μA.cm$^{-2}$ and a non-working voltage of 552 mV.

The modified rhodamine B used above was obtained in the following way:

5 mmol of the potassium salt of trifluoromethanesulfonic acid $CF_3SO_3K$ were added to 5 mmol of sulforhodamine B (sold by Aldrich) in 15 ml of anhydrous dimethylformamide. After stirring for two hours, 10 mmol of oxalyl chloride ClCOCOCl, in solution in 10 ml of anhydrous dichloromethane, were slowly added. The reaction was continued overnight under argon and then 20 mmol of the potassium salt ($CH_3$)$_2NSO_2CHKSO_2CF_3$, prepared as in Example 3, were added. After 48 hours, the dimethylformamide was evaporated and the residue was recrystallized from 40 ml of water. After filtering and drying, the expected product was obtained:

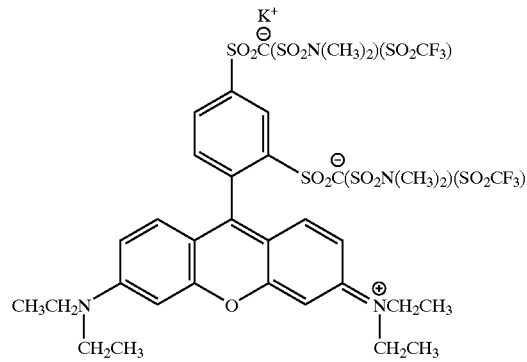

A supercapacitor was also prepared by using the molten salt of the present example as electrolyte and, as electrodes, carbon/aluminum composite electrodes. The electrodes, with a thickness of 150 μm, were placed on either side of a microporous polyethylene film with a thickness of 40 μm and the complete system sealed, in a glove box, in a button cell case. The supercapacitor thus obtained made it possible to carry out more than 100,000 charging/discharging cycles between 0 and 2.5 V for an energy density of greater than 25 Wh/l and a delivered power of greater than 1500 W/l.

The lithium salt [($CH_3$)$_2NSO_2$]$_2CLiSO_2CF_3$, prepared according to the procedure of Example 1, was dissolved in the molten salt of the present example at a concentration of 0.5M. The composition thus obtained was used as electrolyte in a battery comprising an anode based on lithium titanate $Li_4Ti_5O_{12}$ and a mixed oxide of cobalt and lithium $LiCoO_2$. This battery gave performances equivalent to [lacuna] a similar battery comprising a liquid electrolyte based on the ethylene carbonate/methyl carbonate (50/50 v/v) mixture comprising 1M $LiPF_6$ as salt.

EXAMPLE 8

The lanthanum salt [($CH_3$)$_2NSO_2$]$_2C(1/3La^{3+})SO_2CF_3$ was obtained by treating the potassium salt obtained in Example 1 with a stoichiometric amount of lanthanum perchlorate $La(ClO_4)_3$ in acetonitrile. After filtering in order to remove the potassium perchlorate precipitate $KClO_4$ and evaporating the solvent, the lanthanum salt was recovered quantitatively.

This salt was used as catalyst of a Diels-Alder reaction, namely the reaction of methyl vinyl ketone with cyclopentadiene, according to a procedure similar to that described by Kobayashi, Nie & Sonoda (*Synlett*. (1996), 171–172) for lanthanum salts of bis(perfluorosulfonyl) imide.

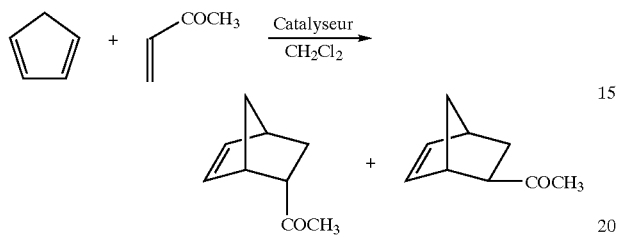

200 μmol of the lanthanum salt were added to a solution, in 10 ml of dichloromethane, of freshly distilled cyclopentadiene (10 mmol) and of methyl vinyl ketone. After 24 hours at room temperature, the reaction mixture was filtered in order to remove the suspended catalyst. A reaction yield, determined by gas chromatography, of greater than 90% was obtained.

EXAMPLE 9

20 mmol of moniliformin (sold by Sigma) were treated with 20 mmol of lithium hydride in 20 ml of anhydrous tetrahydrofuran. After stirring for 2 hours, 25 mmol of trifluoromethanesulfonyl fluoride (sold by Apollo, United Kingdom) were bubbled through over a period of one hour. After stirring for 24 hours, the reaction mixture was filtered, the solvent evaporated and the residue dried. The following lithium salt was thus obtained:

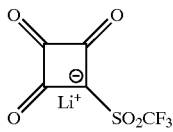

This solvent exhibits good solubility in the usual organic solvents (tetrahydrofuran, acetonitrile, dimethylformamide, ethyl acetate, glymes, and the like) and in aprotic solvating polymers, such as poly(ethylene oxide).

What is claimed is:

1. Ionic composition comprising at least one ionic compound in solution in a solvent, the said compound comprising an anionic part associated with at least one cationic part $M^{m+}$ in a number sufficient to ensure the electronic neutrality of the compound, the said composition being characterized in that it has a conductivity of greater than $10^{-5}$ S.cm$^{-1}$ at a temperature of between $-30°$ C. and $150°$ C., in that $M^{m+}$ is selected from the group consisting of: a proton, a hydronium, a hydroxonium, a nitrosonium $NO^+$, an ammonium —$NH_4^+$ and a cation having the valency m selected from the group consisting of: metal cations, organic cations and organometallic cations, and in that the anionic part corresponds to the formulae

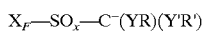

in which:

x is 1 or 2;

$X_F$ represents a perhalogenated radical selected from the group consisting of: alkyl, alkylaryl, oxa-alkyl, aza-alkyl, thia-alkyl, alkenyl, oxa-alkenyl, aza-alkenyl, thia-alkenyl, dialkylazo, and organic radicals in which the carbon α to the $SO_x$ group carries at least one F atom;

Y or Y' represent a sulfonyl, sulfinyl, carbonyl or phosphonyl group;

R is an organic radical and R' is H or an organic radical, wherein said organic radicals are selected independently from a group consisting of alkyl, alkenyl, oxa-alkyl, oxa-alkenyl, aza-alkyl, aza-alkenyl, thia-alkyl, thia-alkenyl and dialkylazo non-halogenated radicals having from 1 to 24 carbon atoms;

aryl, arylalkyl, alkylaryl and alkenylaryl non-halogenated radicals having from 5 to 24 carbon atoms;

non-halogenated radicals which possess at least one anionic ionophoric group;

non-halogenated radicals which comprise at least one ethylenic unsaturated group, one condensable group, or one group dissociable by a thermal route;

non-halogenated radicals which comprise a mesomorphic group, a chromophoric group, a self doped electronic conducting polymer, or a hydrolyzable alkoxysilane; and non-halogenated radicals which comprise a group capable of scavenging free radicals, a dissociating dipole, a redox couple, a complexing ligand, an optically active group, an optically active polypeptide and a biologically active polypeptide;

with the proviso that each of the substituents R and R' is unlinked, a part of an aromatic or nonaromatic ring, or part of a polymer.

2. Ionic composition according to claim 1, characterized in that the cation of the ionic compound is a metal cation selected from the group consisting of: alkali metal cations, alkaline earth metal cations, transition metal cations in the divalent or trivalent state, and rare earth metal cations.

3. Ionic composition according to claim 1, characterized in that $X_F$ is selected from the group consisting of: a perhalogenated alkyl radical having from 1 to 12 carbon atoms and a perhalogenated alkylaryl radical having from 6 to 9 carbon atoms.

4. Ionic composition according to claim 1, characterized in that $X_F$ is selected from the group consisting of $R^HCF_2$—, $R^HCF_2CF_2$—, $R^HCF_2CF(CF_3)$— and $CF_3C(R^H)F$—, wherein $R^H$ represents a nonperhalogenated organic radical.

5. Ionic composition according to claim 1, characterized in that two R and R' substituents together form a divalent radical connected to a Y group and a Y' group.

6. Ionic composition according to claim 4, characterized in that R, R' or $R^H$ represent, independently of one another, an alkyl radical having from 1 to 12 carbon atoms or an alkenyl radical having from 2 to 12 carbon atoms.

7. Ionic composition according to claim 1, characterized in that R and R' together form a biradical connected, at each of its ends, to an —$SO_2$—$C^-SO_2X_F$ anionic group.

8. Ionic composition according to claim 1, characterized in that an R, or an R' substituent is a polymer radical.

9. Composition according to claim 1, characterized in that an R or R' substituent is a recurring unit of a polymer.

10. Ionic composition according to claim 1, characterized in that the solvent of the ionic composition is selected from the group consisting of: an aprotic liquid solvent, a polar polymer and one of their mixtures.

11. Ionic composition according to claim 10, characterized in that the aprotic liquid solvent is chosen from the group consisiting of linear ethers and cyclic ethers, esters, nitriles, nitro derivatives, amides, sulfones, sulfolanes, alkylsulfamides and partially halogenated hydrocarbons.

12. Ionic composition according to claim 10, characterized in that the solvent is a solvating polymer.

13. Ionic composition according to claim 10, characterized in that the solvent is a solvating polymer selected from the group consisting of:

polyethers having one of: a linear structure, a comb structure and a block structure, copolymers selected from the group consisting of: ethylene oxide, propylene oxide and allyl glycidyl ether unit, polyphosphazenes, one of: crosslinked networks based on poly(ethylene glycol) crosslinked by isocyanates and networks obtained by polycondensation and carrying groups which make possible the incorporation of crosslinked groups, and block copolymers in which some blocks carry functional groups which have redox properties.

14. Ionic composition according to claim 10, characterized in that the solvent comprises an aprotic liquid and a polar polymer comprising units comprising at least one heteroatom chosen from the group consisting of sulfur, nitrogen, oxygen and fluorine.

15. Ionic composition according to claim 1, further comprising a second salt.

16. Ionic composition according to claim 1, further comprising a filler selected from the group consisting of a powder and fibers.

17. Electrochemical device, further comprising, as electrolyte, an ionic composition according to claim 1.

18. Ionic composition according to claim 4, characterized in that R and R' together form a biradical connected, at each of its ends, to an —$SO_2$—$C^-SO_2X_F$ anionic group.

19. Ionic composition according to claim 4, characterized in that an R, R' or $R^H$ substituent is a polymer radical.

20. The ionic composition according to claim 1, characterized in that $X_F$ is a monovalent radical.

21. The ionic composition according to claim 1, characterized in that $X_F$ is a multivalent radical.

22. The ionic composition according to claim 1, characterized in that $X_F$ is a multivalent radical connected to more than one —$SO_xC$— group.

23. The ionic composition according to claim 1, characterized in that $X_F$ is a linear radical.

24. The ionic composition according to claim 1, characterized in that $X_F$ is a branched radical.

25. The ionic composition according to claim 1, characterized in that $X_F$ is a cyclic radical.

26. The ionic composition according to claim 1, characterized in that R is a monovalent radical.

27. The ionic composition according to claim 1, characterized in that R' is a monovalent radical.

28. The ionic composition according to claim 1, characterized in that R is a multivalent radical.

29. The ionic composition according to claim 1, characterized in that R' is a multivalent radical.

30. The ionic composition according to claim 1, characterized in that R is a multivalent radical which possess at least one anionic ionophoric group and at least one cationic ionophoric group.

31. The ionic composition according to claim 1, characterized in that R' is a multivalent radical which possess at least one anionic ionophoric group and at least one cationic ionophoric group.

32. The ionic composition according to claim 1, characterized in that each of the substituents $X_F$, R and R' is connected to a different one of the substituents carried by the same anionic center C.

33. The ionic composition according to claim 3, characterized in that $X_F$ has no heteroatom.

34. The ionic composition according to claim 3, characterized in that $X_F$ has a heteroatom selected from the group consisting of: O, N and S.

35. The ionic composition according to claim 34, characterized in that the heteroatom is between two carbon atoms.

36. The ionic composition according to claim 34, characterized in that the heteroatom is at the end of the radical $X_F$.

37. The ionic composition according to claim 6, characterized in that R, R' and $R^H$ do not include a heteroatom.

38. The ionic composition according to claim 6, characterized in that at least one of R, R' or $R^H$ include a heteroatom selected from the group consisting of: O, N and S.

39. The ionic composition according to claim 38, wherein the heteroatom is in a main chain.

40. The ionic composition according to claim 38, wherein the heteroatom is in a side chain.

41. The ionic composition according to claim 6, characterized in that at least one of R, R' or $R^H$ carry at least one of: a hydroxyl group, a carbonyl group, an amine group, an alkoxysilane group, and a carboxyl group.

42. Ionic composition according to claim 12, characterized in that the solvent is crosslinked.

43. Ionic composition according to claim 12, characterized in that the solvent is noncrosslinked.

44. Ionic composition according to claim 12, characterized in that the solvent carries grafted ionic groups.

45. Ionic composition according to claim 12, characterized in that the solvent does not carry grafted ionic groups.

46. Ionic composition according to claim 10, characterized in that the solvent is a polyether forming a network based on poly(ethylene oxide).

47. Ionic composition according to claim 10, characterized in that the solvent is a polyether not forming a network based on poly(ethylene oxide).

48. Ionic composition according to claim 16, characterized in that the filler is an organic filler.

49. Ionic composition according to claim 16, characterized in that the filler is an inorganic filler.

* * * * *